United States Patent [19]

Griesbach, III

[11] Patent Number: 5,506,277
[45] Date of Patent: Apr. 9, 1996

[54] STARCH FOAMS FOR ABSORBENT ARTICLES

[75] Inventor: Henry L. Griesbach, III, Atlanta, Ga.

[73] Assignee: Kimberly-Clark Corporation, Neenah, Wis.

[21] Appl. No.: 268,681

[22] Filed: Jun. 30, 1994

[51] Int. Cl.$^6$ .................................................. C08J 9/00
[52] U.S. Cl. ............................................ 521/84.1; 521/149
[58] Field of Search ................................. 521/84.1, 149

[56] References Cited

U.S. PATENT DOCUMENTS

| | | | |
|---|---|---|---|
| 3,347,236 | 10/1967 | Torr | 128/284 |
| 3,610,245 | 10/1971 | Bernardin et al. | 128/290 |
| 3,661,154 | 5/1972 | Torr | 128/284 |
| 3,981,100 | 9/1976 | Weaver et al. | 47/58 |
| 4,055,184 | 10/1977 | Karami | 128/287 |
| 4,059,114 | 11/1977 | Richards | 128/287 |
| 4,394,930 | 7/1983 | Korpman | 220/444 |
| 4,454,268 | 6/1984 | Otey et al. | 524/47 |
| 4,504,602 | 3/1985 | O'Connell et al. | 521/84.1 |
| 4,673,438 | 6/1987 | Wittwer et al. | 106/126 |
| 4,690,679 | 9/1987 | Mattingly, III et al. | 604/383 |
| 4,692,473 | 9/1987 | Wright et al. | 521/84.1 |
| 4,847,141 | 7/1989 | Pazos et al. | 428/226 |
| 4,863,655 | 9/1989 | Lacourse et al. | 264/53 |
| 4,985,467 | 1/1991 | Kelly et al. | 521/52 |
| 5,035,930 | 7/1991 | LaCourse et al. | 521/84.1 |
| 5,043,196 | 8/1991 | LaCourse et al. | 521/84.1 |
| 5,064,653 | 11/1991 | Sessions et al. | 424/445 |
| 5,079,354 | 1/1992 | Gross et al. | 536/111 |
| 5,095,054 | 3/1992 | Lay et al. | 524/47 |
| 5,106,880 | 4/1992 | Miller et al. | 521/54 |
| 5,147,343 | 9/1992 | Kellenberger | 604/368 |
| 5,153,037 | 10/1992 | Altieri | 428/35.6 |
| 5,185,009 | 2/1993 | Sitnam | 604/364 |
| 5,208,267 | 5/1993 | Neumann et al. | 521/79 |
| 5,219,646 | 6/1993 | Gallagher et al. | 428/287 |
| 5,288,765 | 2/1994 | Bastioli et al. | 521/84.1 |
| 5,352,709 | 10/1994 | Tarrout et al. | 521/84.1 |
| 5,360,830 | 11/1994 | Bostioli et al. | 521/84.1 |

FOREIGN PATENT DOCUMENTS

| | | |
|---|---|---|
| 632971 | 1/1993 | Australia . |
| 87847 | 9/1983 | European Pat. Off. . |
| 121952 | 10/1984 | European Pat. Off. . |
| 409782A2 | 1/1991 | European Pat. Off. . |
| 425270 | 5/1991 | European Pat. Off. . |
| 447792 | 9/1991 | European Pat. Off. . |
| 55-048214 | 4/1980 | Japan . |
| 57-145151 | 9/1982 | Japan . |
| 1731229A1 | 5/1992 | U.S.S.R. . |
| 1550614 | 8/1979 | United Kingdom . |
| 1570485 | 7/1980 | United Kingdom . |

*Primary Examiner*—Morton Foelak
*Attorney, Agent, or Firm*—Michael U. Lee

[57] ABSTRACT

The present invention provides a resilient absorbent foam containing starch, a superabsorbent material and a plasticizer. The absorbent foam is highly absorbent, dimensionally stable, resilient and flexible as well as biodegradable and flushable. Additionally provided is an absorbent foam comprising starch and a plasticizer, which is highly resilient and flexible. The present invention also provides an absorbent article containing the resilient absorbent foam.

8 Claims, 4 Drawing Sheets

1

STARCH FOAMS FOR ABSORBENT ARTICLES

BACKGROUND OF THE INVENTION

The present invention is related to an absorbent material for absorbent articles. More particularly, the present invention is related to an absorbent material fabricated from starch.

Absorbent articles containing an absorbent core, e.g., diapers and sanitary napkins, are widely utilized. In general, such products have an absorbent core which contains one or more layers of fluid absorbent materials, such as fluffed cellulose batt, e.g., wood pulp, cotton fluff, tissue and the like. The absorbent core may additionally contain particles of a superabsorbent. Superabsorbents are hydrocolloids that absorb at least about 10 times its own weight of aqueous fluid. Since superabsorbents are relatively expensive, provide only weak structural integrity and require high surface area to be efficient, they are in general employed as small particulates that are dispersed or imbedded in a matrix of fluffed cellulosic fiber batt, e.g., wood or cotton fluff, or in a thermoplastic foam, e.g., polyurethane foam.

However, these prior art approaches in incorporating a superabsorbent into an absorbent core have disadvantages. For example, superabsorbent particles dispersed in a fluffed cellulosic fiber batt may settle over time, altering the absorption performance and deviating from the designed criteria of the absorbent article. In addition, the fiber batt tends to collapse and close interfiber-capillaries when the batt is expose to liquid, thereby hindering subsequent insults of liquid from having an access to unused portions of the batt and the superabsorbent particles dispersed therein. Furthermore, since superabsorbent particles must be allowed to swell for the particles to efficiently absorb liquid, the collapsed batt which hinders the expansion of the superabsorbent particles prevents efficient use of the particles. An example of such absorbent-hinderance problems is addressed in U.S. Pat. No. 5,147,343 to Kellengerger.

As for dispersing superabsorbent particles in a polyurethane foam, the inherent hydrophobic nature and rigidity of the polyurethane foam cause inefficient use of the absorbent materials. The intercellular structure of the foam may not provide sufficiently large enough space to allow the superabsorbent particles to fully swell, causing an inefficient use of the absorbent capacity of the superabsorbent particles. Moreover, as disclosed for example in U.S. Pat. No. 4,985, 467 to Kelly et al., the intercellular structure of the inherently hydrophobic foam must be carefully engineered to allow liquid to have proper access to the imbedded superabsorbent particles.

Consequently, it would be desirable to provide an economical and highly efficient superabsorbent-containing absorbent material that does not have the above-illustrated disadvantages of the prior art absorbent materials.

SUMMARY OF THE INVENTION

There is provided in accordance with the present invention a resilient absorbent foam containing starch, a superabsorbent material and a plasticizer. The absorbent foam is a highly absorbent article that additionally provides high dimensional stability, resiliency and flexibility. In addition, the foam absorbent article is biodegradable and flushable. Additionally provided is an absorbent foam containing starch and a plasticizer, which is highly resilient and flexible.

The present invention also provides an absorbent article containing the resilient absorbent foam. The absorbent article is suitable for application where the article is subjected to multiple insults of liquid inflows. The article does not contain the conventional carrier cellulose fluff for superabsorbents, which tends to collapse upon a liquid insult and hinders the full utilization of the absorbent capacity of the superabsorbent, so that the superabsorbent dispersed in the foam absorbent is efficiently utilized.

The foam absorbent is highly suitable for use in absorbent articles, such as diapers, sanitary napkins, adult care products, wound dressings and the like.

DETAILED DESCRIPTION OF THE INVENTION

Figure 1:
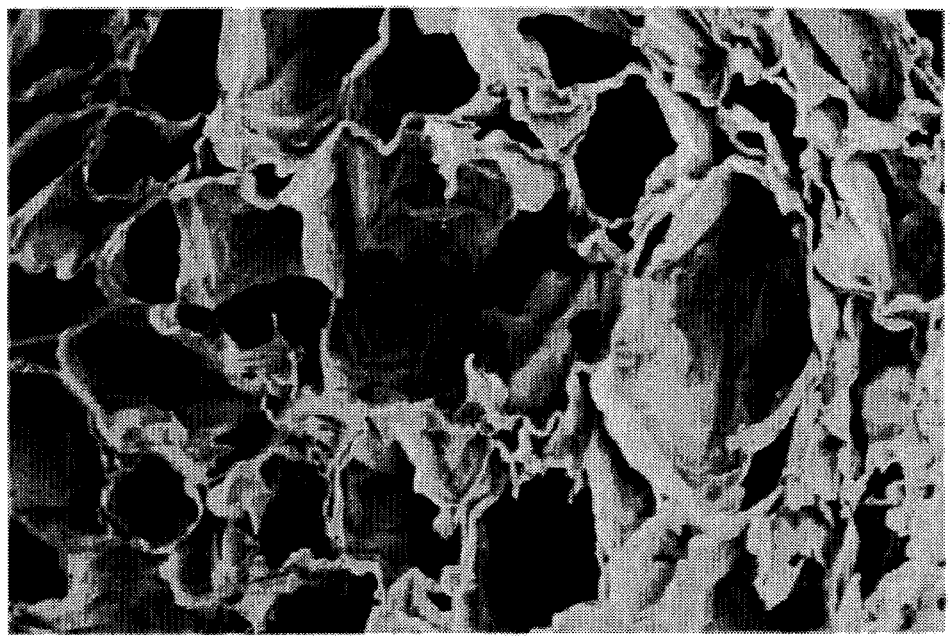
FIG. 1 is a 20 times magnified view of a starch foam of the present invention, showing the closed cell structure.

The present invention provides an economical and efficient absorbent material suitable for use in absorbent articles, such as diapers, sanitary napkins, adult care products, wound dressings and the like. The absorbent material is a starch foam produced from a starch blend composition. The starch blend composition contains, based on the total weight of the composition, from about 20 wt % to about 80 wt %, desirably from about 25 wt % to about 70 wt %, more desirably from about 30 wt % to 50 wt %, of starch; up to about 70 wt %, desirably from about 5 wt % to about 60 wt %, more desirably from about 10 wt % to about 50 wt %, most desirably from about 20 wt % to about 40 wt %, of a superabsorbent; and from about 5 wt % to about 40 wt %, desirably between about 10 wt % and 30 wt %, more desirably between 15 wt % and about 25 wt %, of a plasticizing agent.

The term starch as used herein indicates reserve polysaccharides found in plants, e.g., corn, wheat, potato and the like, and is a mixture of linear (amylose) and branched (amylopectin) polymers of α-D-glucopyranosyl units. As is known in the art, natural starches from different plants contain different levels of amylose and amylopectin. Although different starches containing different levels of the two glucopyranosyl units can be employed for the present absorbent material, desirable starches contain at least about 20 wt %, more desirably at least about 25 wt %, based on the total starch weight, of amylose. In general, high amylose content starch provides a more resilient starch foam.

Superabsorbents suitable for the present invention include natural or synthetic ionic hydrocolloids and nonionic hydrocollids that are water insoluble but water swellable polymer solids, e.g., polyacrylamides, polyarylic acids, metal salts of polyacrylic acid, polyacrylates, polymers and copolymer of vinyl sulfonic acid, polyacrylate grafted starches, polyvinyl ethers, polyvinylpyrrolidone, sulfonated polystyrene polysulfoethyl acrylate, and the like. Additionally suitable superabsorbents are starch and cellulose based superabsorbents, including carboxymethyl starch, carboxymethyl cellulose and saponified starch-polyacrylonitrile graft copolymers. Of these, more desirable superabsorbent materials are metal salts, e.g., sodium salt, of polyacrylic acids.

The starch foam of the present invention further contains a polymeric plasticizing agent or plasticizer to provide improved flexibility and resiliency. Suitable plasticizing agents must have a sufficient thermal stability to withstand the temperature of the foam production process and do not significantly interfere with the absorbent property of the foamed starch. Plasticizing agents suitable for the present starch composition include polyvinyl alcohol, ethylene vinyl alcohol copolymer, polyvinyl acetate, ethylene vinyl acetate and blends thereof. Of the suitable plasticizing agents, polyvinyl alcohol is particularly desirable. Specifically, polyvinyl alcohol suitable for the present invention has a molecular weight of from about 25,000 to about 190,000, desirably from about 30,000 to about 150,000, and a degree of hydrolysis of at least about 70%, desirably from about 85% to about 99%.

Suitable starch foams of the present invention are produced when the starch composition with a defined amount of water is treated at an elevated temperature in a closed container to form a pressurized melt and then the melt is exposed to an environment that allows the melt to expand and cool, e.g., ambient environment. This foaming process can be conveniently carried out in an extruder, particularly in an unvented extruder, which is equipped with a heating jacket or heating element. Extruders useful for the present invention include conventional single-screw and twin-screw extruders, although twin-screw extruders are more desirable in that they promote more thorough mixing of the starch foam composition. The temperature and pressure of the extruder are controlled to process the starch composition at an elevated temperature, which may be between about 100° C. and about 200° C., desirably between about 110° C. and about 150° C., and at an elevated pressure, which may be between about 500 psi and about 1,300 psi. The starch composition is fed to an extruder and gradually becomes molten while the water content of the composition becomes superheated as the composition is passed through the conveying zone and the compression zone of the extruder. The molten starch composition is then conveyed to and extruded through a die to form shaped foam articles. The die opening may have any desired configuration to produce shaped foam articles that are suitable for absorbent articles, e.g., sheets and rods. As the molten starch containing compressed, superheated water is extruded and exposed to a lower pressure and temperature environment, e.g., ambient environment, the molten starch expands while approximately retaining the circumferential contour of the opening of the die and solidifies to produce a foam material having a closed cell structure. The extruded foam articles from the present starch composition have a relatively uniform closed cell structure with low density and good resiliency, flexibility and dimensional stability. The flexibility and resiliency of the articles can be further improved by calendering or flexing the extruded foam articles. Alternatively, the starch composition can be extruded into pellets. The pellets can be subsequently molded into an absorbent foam article in a mold by packing the mold with the pellets and exposing the pellets to humidity, e.g., a stream of steam or mist, under moderate pressure to form a fused, shaped absorbent structure. It has been found that the present starch foam pellets are highly shapable and fusible without losing the closed cell structure and absorbent capacity when the foam pellets, more specifically exterior surfaces of the pellets, are moistened. During the molding process, heat may be applied to dry or remove moisture from the fused, shaped absorbent article.

In order to obtain proper starch foam structures, the total moisture content of the starch composition should be from about 5 to about 30 weight %, more preferably from about 9 to about 20 weight %, most preferably from about 14 to about 17 weight %, based on the dry weight of starch in the composition. Typically, commercially produced starch contains about 7 to 12% by weight residual moisture. Therefore, little or no addition of water is required to produce the present starch foam absorbent material.

Surprisingly, it has been found that subjecting the superabsorbent through the extrusion process does not measurably diminish its absorbent capacity and that the starch foam structure integrally and securely incorporates the superabsorbent. The starch foam which has the superabsorbent uniformly and securely dispersed therein is highly suitable for the absorbent layer of absorbent articles. Unlike the prior art foam matrices holding superabsorbent particles, e.g., polyurethane foam, the starch foam matrix does not significantly impede the swelling movement of the dispersed superabsorbent since the foamed starch itself is highly water absorbent and becomes highly malleable and deformable upon absorbing liquid. In addition, the dispersed superabsorbent, which is securely incorporated into the cell wall of the starch foam, does not dislodge from the foam.

Figure 2:
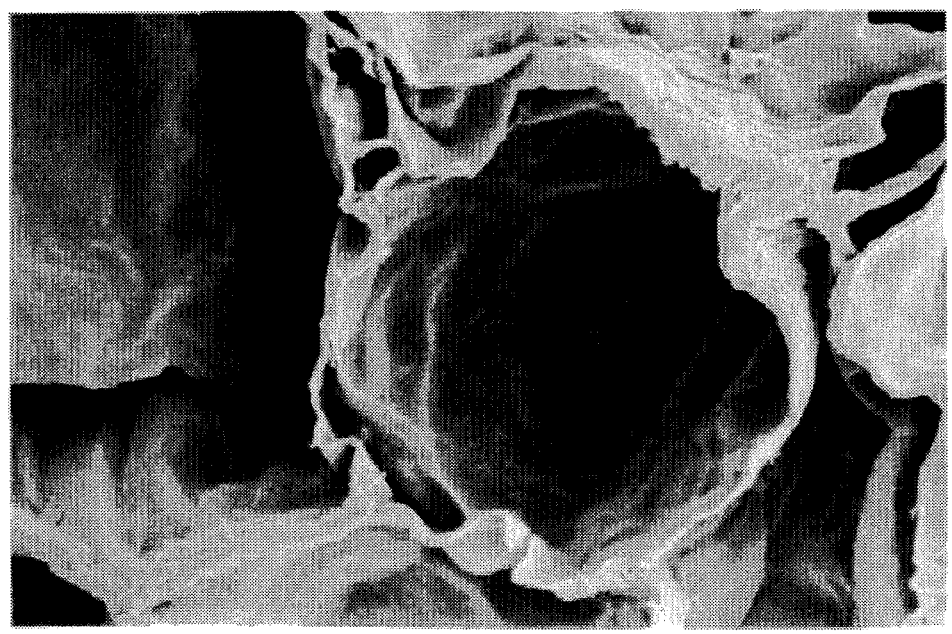
FIG. 2 is a 100 times magnified view of the starch foam of FIG. 1, showing the domains of a superabsorbent within the cell walls of the foam.
Figure 3:
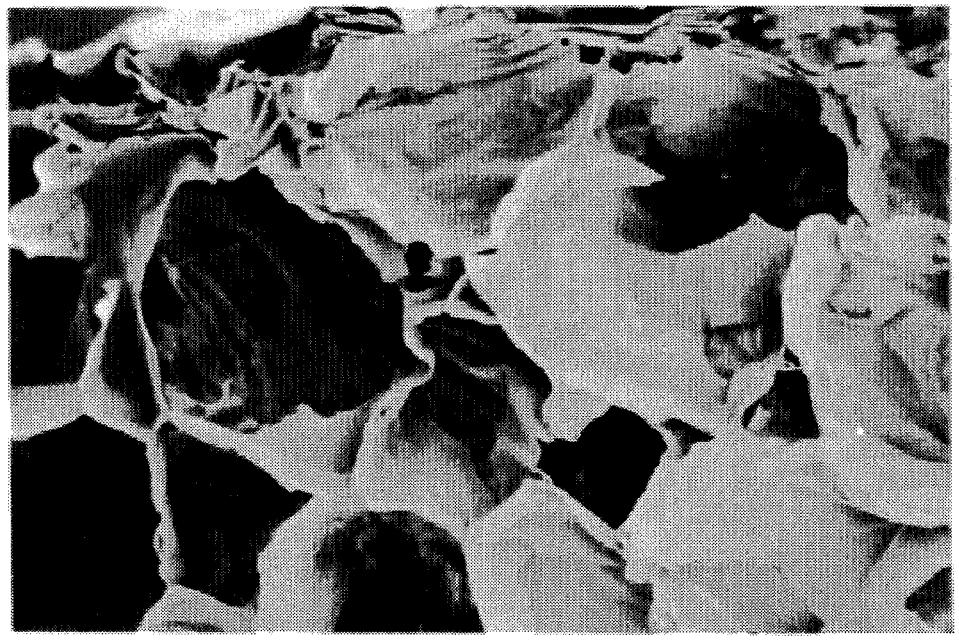
FIG. 3 is a 20 times magnified view of a starch foam that contains starch and a plasticizing agent.
Figure 4:
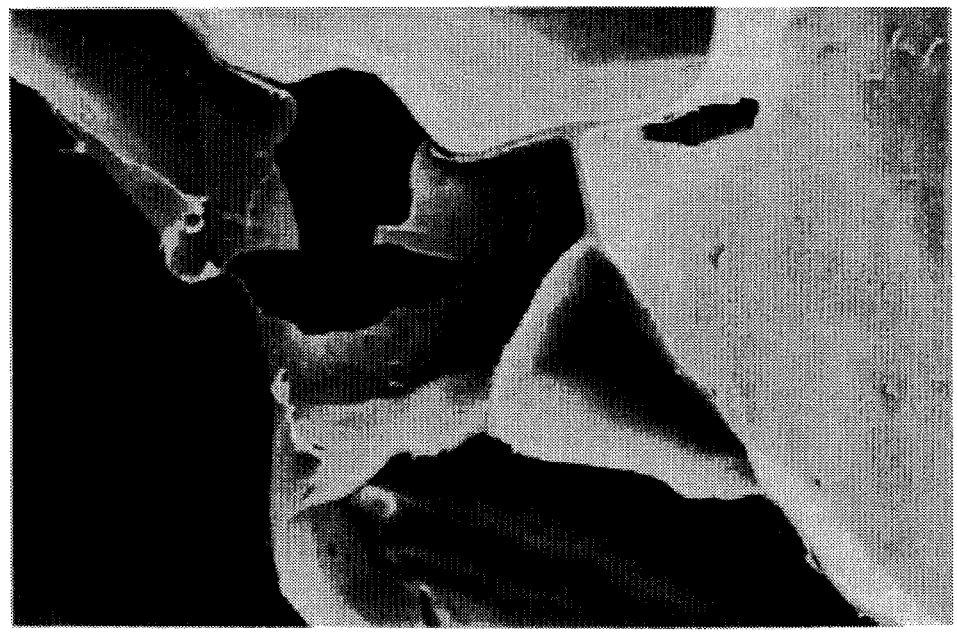
FIG. 4 is a 100 times magnified view of the starch foam of FIG. 3.

Turning to the figures, FIGS. 1–2 are magnified views of an exemplary absorbent material of the present invention, and FIGS. 3–4 are magnified views of a starch foam, Example 14, infra, that is produced from a starch composition which contains starch and a plasticizing agent. As will be further described in Example 2, the foam composition of FIGS. 1 and 2 contains about 57 wt % of starch, 23 wt % of a superabsorbent and 20 wt % of a plasticizing agent. FIGS. 1 and 3, which are 20 times magnified views, show the closed cell structure of the present starch foam, and FIGS. 2 and 4, which are 100 times magnified views, show the starch foam structure in greater detail. FIG. 2, when compared to FIG. 4, shows thick and rough sections in the cell structure of the foam, and these sections are believed to be the superabsorbent dispersed in the starch matrix. As can be seen from FIG. 2, the superabsorbent is securely incorporated into the starch foam matrix as an integral part of the foam structure, forming well disbursed and permanently integrated superabsorbent domains throughout the wall of the foam structure.

Additional advantages of the starch foam absorbent material, which is derived from natural starch, include that the foam matrix is highly biodegradable and provides limited integrity and resiliency when wetted with saline solutions. Consequently, the absorbent material, especially when a starch-based superabsorbent is utilized therein, is highly biodegradable, alleviating the disposal problem. In addition, an application of limited agitation or force disintegrates the liquid saturated starch foam into small pieces or segments that can easily be composted or flushed.

Figure 5:
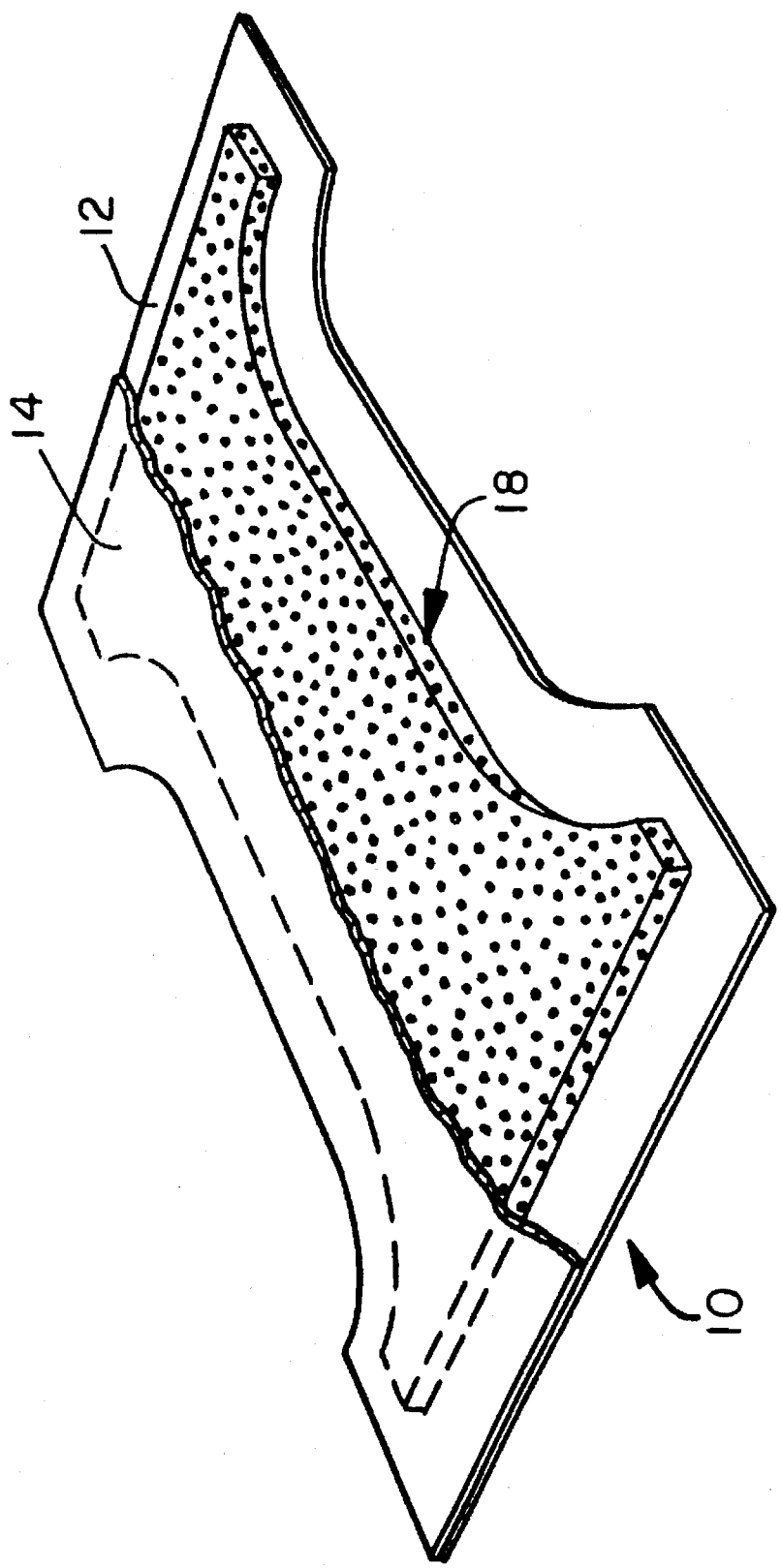
FIG. 5 is an absorbent article containing a starch foam absorbent core.

The starch foam absorbent material in its unwetted form is a highly flexible and resilient absorbent material and, thus, is useful for various absorbent articles, including diapers, sanitary napkins, training pants, incontinence products, wound dressings, absorbent layers for meat-trays and the like. For example, the starch foam absorbent material is extruded into a sheet and placed between a liquid-impermeable backing material and a liquid-permeable facing material to form an absorbent article. Turning to FIG. 5, there is provided an absorbent article 10, such as a diaper, containing a liquid-impermeable backing material 12, a liquid-permeable facing material 14 and a starch foam absorbent layer 16. The absorbent layer 16 is formed from the present absorbent starch foam and can be in the form of, for example, a shaped sheet. The starch foam sheet may, in addition, be perforated or apertured to increase the surface area of the absorbent layer, thereby further improving the speed of liquid intake. The liquid-impermeable backing material 12 can be a film produced from a thermoplastic, such as polyethylene, polypropylene, polyester, polyamide, polyvinyl chloride and the like. Alternatively, the backing material can be a microporouos film or a highly liquid-resistant nonwoven fabric that is impervious to liquid but pervious to vapor, thereby increasing the comfort of the user of the absorbent article. The liquid-permeable facing material 14 can be a nonwoven or woven fabric, perforated film or nonwoven, or any other relatively porous material that is known to rapidly pass fluid to the absorbent material.

In accordance with the present invention, the starch composition desirably is thoroughly preblended, for example, in a tumble blender, before the composition is fed to the extruder. The starch foam composition may further contain various additive such as processing aids, lubricants, crosslinking agents, blowing agents, pigments, fillers, reinforcement fibers and the like. Suitable lubricants and processing aids include metal stearates, paraffinic waxes, vegetable and mineral oils, glycerine, glyceryl esters, e.g., glyceryl monostearate, and the like. Suitable filler fibers that improve the strength of the starch foam include cellulosic fibers, e.g., beet fibers, soy fibers, fine pulp fibers and the like.

It is to be noted that although the composition for the present absorbent material is described to contain a superabsorbent, a highly useful absorbent material, although it is not as absorbent as the above-described absorbent material, can be produced in accordance with the present invention without the addition of a superabsorbent since natural starch foam itself readily absorbs aqueous fluids. Such absorbent foam can be produced from a starch composition containing, based on the total weight of the composition, from about 60 wt % to about 90 wt % of starch and from about 40 wt % to about 10 wt % of the above-described plasticizing agent as well as the above-illustrated processing aids and other additives.

The following examples are provided for illustration purposes and the invention is not limited thereto.

EXAMPLES

Examples 1–14

Absorbent starch foam sheets were produced from starch compositions as disclosed in Table 1. In addition, each starch composition contained about 0.5 wt % of an edible vegetable oil, about 0.5 wt % of glycerine and about 0.3 wt % of glyceryl monostearate, Myvaplex™, which is available from Eastman Chemical Products, Inc., as processing aids.

The components of each starch composition were thoroughly blended and then extruded through a Wenger TX-52 twin-screw extruder, having four zones and a die. The four zones were a feeding zone, which was set at about 24° C., a mixing zone, which was set at about 24° C., a conveying zone, which was set at about 24° C. and a compression zone, which was set at about 125° C. The die, which had two circular openings of a 0.08 inch diameter, was set at about 110° C. The feed rate was about 100 lbs/hour.

The resulting starch foam was weighed and then immersed in water for 3 minutes. The water saturated foam was placed on a porous wire screen of a vacuum apparatus for 1 minute to drain excess water. The vacuum apparatus was equipped with a porous wire screen on the top and a neoprene lid that contiguously covers the wire screen and closes the vacuum apparatus. Then the lid was closed and 0.5 psi vacuum pressure was applied for 5 minutes. The weight of the foam was then measured and the absorbent capacity of the foam was calculated as follows: (weight of wet foam—weight of dry foam)/weight of dry foam. The result is shown in Table 1.

TABLE 1

| | | Composition (weight %) | | | | |
|---|---|---|---|---|---|---|
| | | Superabsorbent | | Plasticizer | | Capacity |
| Example | Starch | Type | Content | Type | Content | (g/g) |
| 1 | 67 | IM | 23 | PV3 | 10 | 11.5 |
| 2 | 57 | IM | 23 | PV3 | 20 | 9.7 |
| 3 | 60 | IM | 20 | PV3 | 20 | 13.6 |
| 4 | 50 | IM | 30 | PV3 | 20 | 13.9 |
| 5 | 40 | IM | 20 | PV3 | 30 | 13.6 |
| 6 | 40 | IM | 20 | PV3 | 40 | 14.5 |
| 7 | 40 | IM | 40 | PV3 | 20 | 15.8 |
| 8 | 40 | FA | 40 | PV3 | 20 | 17.1 |
| 9 | 60 | IM | 20 | PV5 | 20 | 13.3 |
| 10 | 50 | IM | 30 | PV5 | 20 | 11.3 |
| 11 | 72 | G4 | 8 | PV3 | 20 | 7.6 |
| 12 | 60 | IM | 20 | EPV | 20 | 6.1 |
| 13 | 80 | IM | 20 | — | 0 | 10 |
| 14 | 80 | — | 0 | PV3 | 20 | 6.3 |

IM = superabsorbent Sandwet ™ IM 5000, which is a polyacrylate superabsorbent and is available from Hoechst Celanese.
FA = superabsorbent Favor ™ 870, which is a polyacrylate superabsorbent and is available from Stockhousen.
G4 = polyacrylate grafted starch superabsorbent Waterlock ™ G400, which is available from Grain Processing.
PV3 = polyvinyl alcohol Airvol ® 325, which is available from Air Products and Chemicals, Inc. and its hydrolysis level is about 98% and molecular weight is between about 85,000 and 146,000.
PV5 = polyvinyl alcohol Airvol ® 540, which is available from Air Products and Chemicals, Inc. and its hydrolysis level is about 88% and molecular weight is between about 124,000 and 186,000.
EPV = ethylene polyvinyl alcohol EVAL ™ 400, which contains about 44 wt % of ethylene. EVAL is available from EVAL Corp of America.

All of the starch foams of the above examples, except Example 13, were resilient as well as aqueous-fluid absorbent, making them highly suitable for absorbent articles. The starch foam of Example 13, which did not contain a plasticizing agent, was a rigid material that was irreversibly compacted and disintegrated into an aggregate of powder or small clumps when pressure was applied.

As stated above and illustrated in FIGS. 1–4, the present starch foam is a resilient absorbent material, and in addition, the starch foam incorporates superabsorbents into its wall matrix, improving the absorbency of the foam and securely holding and evenly distributing the superabsorbents throughout the matrix.

Example 15

A foam sheet was produced from the starch composition of Example 2 by extruding the composition at 460 lbs/hr through a Wenger TX-80 twin-screw extruder equipped with a 1 mm by 100 mm slot die. The configuration and the temperature profile of the extruder were as described in Example 2. The resulting foam sheet was compacted to form an absorbent structure having enhanced flexibility and resiliency. A flat press was used to apply a 10,000 lbs force on a sheet having an about 4 inch width and an about 12 inch length to reduce the thickness of the sheet to about 6% of its initial thickness. The compacted starch foam exhibited improved resiliency and flexibility over the uncompacted starch foam.

The compressed sheet recovered its thickness to about 30% of the original thickness within about 35 minutes in ambient environment. The absorbent capacity of the compressed sheet was tested and found that there was no measurable change in the capacity. The recovery of the compressed specimen demonstrates the resiliency of the present foam absorbent article when compared to the irreversible destruction of the starch foams that do not contain the polymeric plasticizing agent, e.g., Example 13.

Figure 6:
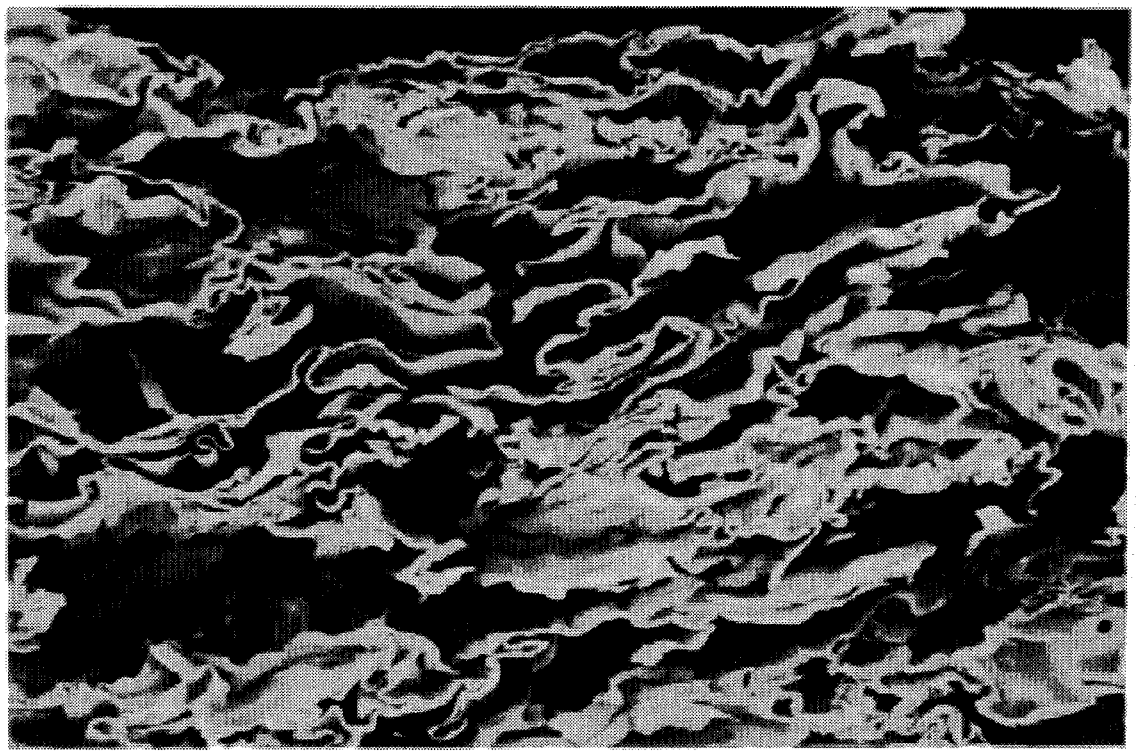
FIG. 6 is a 20 times magnified view of a starch foam of the present invention that was compacted to impart improved flexibility and resiliency.

Turning to the figures, FIG. 6 is a 20 times magnified view of the cross-section of the compacted starch foam of Example 15. FIG. 6 shows that the compacted starch foam retains the cellular structure, although the cells were compressed and some of the cell walls were ruptured, demonstrating the resiliency of the cellular structure and, thus, of the present starch foam.

Example 16

The foam composition of Example 1 was prepared and extruded in accordance with Example 1, except a pelletizing die having two 0.08 inch circular openings equipped with a face-pelletizer was used to produce cylindrical foam pellets having a length of about 0.5 inches and a diameter of about 0.375 inches.

Subsequently, 5.3 g of the pellets were sprayed with 1.5 ml of water using a water spray bottle and then loosely placed in a cylindrical mold having an inner diameter of about 3 inches, which pellets filled to a height of about 3.5 inches. The pellets in the mold were compressed to a height of about 0.75 inches using a flat, cylindrical plunger to allow the wetted pellets to get in contact with one another to form a fused, unitary structure. The fused, molded article was then dried. The resulting unitary foam ariticle was resilient and retained the absorbency and the closed cell structure of the foam pellets.

What is claimed is:

1. A resilient absorbent foam comprising starch, a superabsorbent material selected from the group consisting of polyacrylamides, polyacrylic acids, metal salts of polyacrylic acid, polyacrylates, grafted starches, polyvinyl ethers, polyvinylpyrrolidone, sulfonated polystyrene, polysulfoethyl acrylate, carboxymethyl starch, carboxymethyl cellulose and saponified starch-polyacrylonitrile graft copolymers and a polymeric plasticizer.

2. The absorbent foam of claim 1 wherein said starch comprises, based on the total weight of the foam, from about 20 wt % to about 80 wt %.

3. The absorbent foam of claim 1 wherein said superabsorbent comprises, based on the total weight of the foam, up to about 70 wt %.

4. The absorbent foam of claim 1 wherein said plasticizing agent comprises, based on the total weight of the foam, from about 5 wt % to about 40 wt %.

5. The absorbent foam of claim 1 wherein said superabsorbent is selected from the group consisting of metal salts of polyacrylic acid.

6. The absorbent foam of claim 1 wherein said plasticizing agent is selected from group consisting of polyvinyl alcohol, ethylene vinyl alcohol copolymer, polyvinyl acetate, ethylene vinyl acetate and blends thereof.

7. The absorbent foam of claim 1 wherein said plasticizing agent is polyvinyl alcohol.

8. The absorbent foam of claim 1 further comprising a processing aid.

\* \* \* \* \*